United States Patent [19]

Stiles et al.

[11] Patent Number: 5,320,962
[45] Date of Patent: Jun. 14, 1994

[54] DNA ENCODING THE HUMAN A1 ADENOSINE RECEPTOR

[75] Inventors: Gary L. Stiles, Chapel Hill; Hongzu Ren; Mark Olah, both of Durham, all of N.C.

[73] Assignee: Duke University, Durham, N.C.

[21] Appl. No.: 918,314

[22] Filed: Jul. 22, 1992

[51] Int. Cl.$^5$ ............................................. C17N 15/12
[52] U.S. Cl. ............................ 435/252.3; 435/320.1; 435/69.1; 536/23.5
[58] Field of Search .................. 435/69.1, 252.3, 320.1; 536/27, 23.5

[56] References Cited

PUBLICATIONS

Nature 311:626–631, Oct. 18, 1984, Leonard et al. Molecular cloning and expression of cDNAs for the human interleukin-2 receptor.
Nature 313:806–810, Feb. 28, 1985, Jacobs et al. Isolation and characterization of gemonic and cDNA clones of human erythroporetin.
J. R. Bunzow et al.; *Cloning and expression of a Rat $D_2$ dopamine receptor cDNA*, Nature 336 pp. 22–29 (1988).
S. Maeda; *Expression of Foreign Genes in Insects Using Baculovirus Vectors*, Ann. Rev. Entomol, 34 pp. 351–372 (1989).
B. Giros, et al.; *Alternative splicing directs the expression of two $D_2$ dopamine receptor isoforms*, Nature, 342 pp. 923–926 (1989).
F. Libert, et al.; *Chromosomal Mapping of A1 and A2 Adenosine Receptors, VIP Receptor, and a New Subtype of Serotonin Receptor*, GENOMICS 11, pp. 225–227 (1991).
David John and Irving H. Fox, *Characteristics of high--affinity and low-affinity adenosine binding sites in human cerebral cortex*, J. Lab Clin Med pp. 401–407 (1985).
H. Nakata et al., *Biochemical and immunological characterization of $A_1$ adenosine receptors purified from human brain membranes*, Eur. J. Biochem., 206, pp. 171177 (1992).
C. Nanoff et al., *The $A_2$ Adenosine Receptor: Guanine Nucleotide Modulation of Agonist Binding is Enhanced by Proteolysis* Molecular Pharamacology 39, 130–135 (1990).
C. Nanoff and G. Stiles, *Solubilization and Characterization of the $A_2$–Adenosine Receptor* Journal of Receptor Research 13, 961–973 (1993).
J. W. Ferkany, et al., *Adenosine A1 Receptors in Mammalian Brain: Species Differences in Their Interactions with Agonists and Antagonists* Drug Development Research 9, 85–93 (1986).
Hiroyasu Nakata, *The Journal of Biological Chemistry* 264, No. 28, 16545–16551 (1989).
Hiroyasu Nakata, *The Journal of Bilogical Chemistry* 265, No. 2, 671–677 (1990).
Mark E. Olah et al., *Federation of European Biochemical Societies* 257, No. 2, 292–296 (1989).
Mark E. Olah et al., *Archives of Biochemistry and Biophysics* 283, No. 2, 440–446 (1990).
Lawrence C. Mahan et al., *Molecular Pharmacology* 40, 1–7 (1991).
Frederick Libert et al., *The EMBO Journal* 10, No. 7, 1677–1682 (1991).
D. R. Sibley et al., "Transfected Mammalian Cell Lines Expressing the A1 Adenosine Receptor", NTIS Field/-Group Codes: 57F, 57B, 57Q 90D (Jun. 5, 1991).
Gary L. Stiles, *The Journal of Biological Chemistry* 267, No. 10, 6451–6454 (1992).
O. Eidelman et al., *Proc. Natl. Acad. Sci, USA* 89, 5562–5566 (1992).
Mark E. Olah et al., *The Journal of Biological Chemistry* 267, No. 15, 10764–10770 (1992).
F. Libert et al.; Cloning and Functional Characterization of a Human A1 Adenosine Receptor, *Biochem. Biophys. Res. Comm.* 187 pp. 919–926 (1992).

*Primary Examiner*—Robert J. Hill, Jr.
*Assistant Examiner*—John D. Ulm
*Attorney, Agent, or Firm*—Bell, Seltzer, Park & Gibson

[57] ABSTRACT

Genomic and complimentary DNA encoding the human $A_1$ adenosine receptor are disclosed, along with vectors and host cells containing the same, oligonucleotides and antisense oligonucleotides directed to the same (particularly antisense oligonucleotides directed to an intron/exon junction), and methods of using the foregoing.

30 Claims, 2 Drawing Sheets

HUMAN A1 AR GENE

DNA ENCODING THE HUMAN A1 ADENOSINE RECEPTOR

The present invention was made with Government support under grant number ROI HL35134 from the National Heart Lung and Blood Institute. The Government has certain rights to this invention.

FIELD OF THE INVENTION

The present invention relates to DNA encoding mammalian $A_1$ adenosine receptors, and particularly relates to intronless complimentary DNA encoding the human $A_1$ adenosine receptor and intron-containing genomic DNA encoding mammalian $A_1$ adenosine receptors.

BACKGROUND OF THE INVENTION

Adenosine is found in all living cells and can be released under appropriate conditions, such as ischemia or anoxia, where it can then act upon adenosine receptors to produce a variety of physiological effects. Adenosine receptors are now known to be integral membrane proteins which bind extracellular adenosine, thereby initiating a transmembrane signal via specific guanine nucleotide binding proteins known as G-proteins to modulate a variety of second messenger systems, including adenylyl cyclase, potassium channels, calcium channels and phospholipase C. See G. Stiles, *Clin. Res.* 38, 10–18 (1990); G. Stiles, *J. Biol. Chem.* 267, 6451–6454 (1992).

Adenosine receptors control a variety of important physiological effects including regulation of heart rate and contractility, regulation of smooth muscle tone in both blood vessels and the gastrointestinal tract, regulation of neurotransmitter release in brain, induction of sedation in the brain and regulation of platelet function. Although much biochemical and pharmacological information has become available on the two main types of adenosine receptors (known respectively as $A_1$ and $A_2$) which inhibit and stimulate adenylyl cyclase, much less information is available about their structure at the RNA and DNA level.

Adenosine receptors can be defined by an agonist potency series which, for the $A_1$ receptor, is R-PIA>-NECA >S-PIA, and which for the $A_2$ receptor is NECA>R-PIA>S-PIA. See R. Olsson and J. Pearson, *Physiol. Rev.* 70, 761–845 (1990). Very recently we have found evidence for a unique $A_1$ adenosine receptor which is expressed in the bovine brain which has a different potency series such that R-PIA is >S-PIA which is >NECA. We have cloned and sequenced this receptor and have begun studies on site-directed mutagenesis to understand the ligand binding site. See M. Olah et al., *J. Biol. Chem.* 267, 10764–10770 (1992). In addition, we have found a new receptor previously not suspected, which we have termed the $A_3$ adenosine receptor. This receptor has likewise been cloned, sequenced and expressed. See F. Zhou et al., *Proc. Natl. Acad. Sci. USA*, in press (1992).

SUMMARY OF THE INVENTION

To date, there has been no information on the genomic structure of any adenosine receptor. Neither has there been any information available on any human adenosine receptor cDNA. Such information is, however, necessary if the genomic structure and activity of the human receptor is to be explored. This information is provided herein.

A first aspect of the present invention is isolated DNA encoding an $A_1$ adenosine receptor selected from the group consisting of: (a) isolated DNA which encodes the human genomic $A_1$ adenosine receptor of SEQ ID NO:6, which isolated DNA contains the DNA sequences given herein as SEQ ID NO:1 and SEQ ID NO:3; (b) isolated human genomic DNA which hybridizes to isolated DNA of (a) above under conditions represented by a wash stringency of 0.3M NaCl, 0.03M sodium citrate, and 0.1% SDS at 60° C., which is at least 65% homologous to the isolated DNA of (a) above (i.e., 65% homologous or more with respect to total DNA sequence; homology with respect to exon sequence alone is about 93% or more), and which encodes a human $A_1$ adenosine receptor; and (c) isolated DNA differing from the isolated DNAs of (a) and (b) above in nucleotide sequence due to the degeneracy of the genetic code, and which encodes a human $A_1$ adenosine receptor.

A second aspect of the present invention is isolated DNA encoding an $A_1$ adenosine receptor selected from the group consisting of: (a) the isolated DNA which encodes a human $A_1$ adenosine receptor and has the DNA sequence given herein as SEQ ID NO:5; (b) isolated DNA which hybridizes to the isolated DNA of (a) above under conditions represented by a wash stringency of 0.3M NaCl, 0.03M sodium citrate, and 0.1% SDS at 60° C., which is at least 93% homologous to isolated DNA of (a) above, and which encodes a human $A_1$ adenosine receptor; and (c) isolated DNA differing from the isolated DNAs of (a) and (b) above in nucleotide sequence due to the degeneracy of the genetic code, and which encodes an $A_1$ adenosine receptor.

A third aspect of the present invention is a recombinant DNA sequence comprising vector DNA and a DNA as given above which encodes an $A_1$ adenosine receptor.

A fourth aspect of the present invention is a host cell containing a recombinant DNA sequence as given above and capable of expressing the encoded $A_1$ adenosine receptor.

A fifth aspect of the present invention is an oligonucleotide (e.g., a polynucleotide 10–200 nucleotides in length, preferably 20–200 nucleotides in length) capable of selectively hybridizing to DNA which comprises a portion of a gene coding for an $A_1$-adenosine receptor as given herein. Such oligonucleotides may comprise fragments of a DNA as given above which encodes an $A_1$ adenosine receptor. Such oligonucleotides may be used in a suitable vector for carrying out homologous recombination. When labelled with a detectable group, such oligonucleotides comprise probes. In one preferred embodiment, such oligonucleotides comprise the introns, fragments of the introns, or hybridize to the introns of, the genomic $A_1$-adenosine receptor DNA disclosed herein (i.e., from 5′ to 3′, the first, second, third, fourth or fifth intron of the genomic $A_1$-adenosine receptor) which selectively hybridize to the introns of a genomic $A_1$-adenosine receptor DNA.

A sixth aspect of the present invention is isolated DNA as given above, and oligonucleotides as given above, configured in antisense for the production of antisense RNA which would interfere with the expression of native $A_1$-adenosine receptor (preferably selected so as to not interfere with the production of other adenosine receptors such as the $A_2$ or $A_3$ adenosine receptor (hereinafter referred to as "antisense DNAs"). Such antisense DNAs may be provided in a vector as given above for transcription in a suitable cell where they then interfere with the production of the $A_1$ adenosine receptor. Preferably, such antisense DNAs are directed to one of the intron-exon junctions of the $A_1$ adenosine receptor genomic DNA, as described herein.

A seventh aspect of the present invention is isolated DNA encoding mutant $A_1$ adenosine receptors in which (a) the receptors have decreased affinity for $A_1$ adenosine receptor agonists and/or antagonists, or (b) the receptors bind $A_1$ adenosine receptor agonists with high affinity but fail to inhibit adenylyl cyclase in cells transfected therewith (in which cells the receptor would, but for the mutation, otherwise be seen inhibit adenylyl cyclase). For the latter, mutations which render the hydrophobic pocket in the fifth transmembrane domain less hydrophobic are particularly preferred.

The DNA sequence information provided herein is valuable for several reasons. First, it is known that it regulates a wide variety of physiological effects and, therefore, has great potential for use as a therapeutic agent in a variety of conditions ranging from manipulation of cardiac function, protection against ischemia, regulation of smooth muscle tone in blood vessels, potential usefulness as an agent in cystic fibrosis, usefulness as a potential agent in treatment of seizure activity. Recent studies have shown that the endogenous release of adenosine during a brief occlusion of a coronary artery leads to the protection of the myocardium from subsequent prolonged ischemic and anoxic events. This work shows that this appears to be mediated specifically via the $A_1$ adenosine receptor. See G. Liu et al., *Circulation* 84, 350-356 (1991); S. Ely and R. Berne, *Circulation* 85, 893-904 (1992). This indicates that manipulation of $A_1$ adenosine receptors through either specific ligand manipulation or through introduction by recombinant DNA techniques of wild-type or mutant receptors into myocardium may provide a protective effect against ischemia.

The foregoing and other aspects of the present invention are explained in detail in the drawings, Examples, and Detailed Description set forth below.

DETAILED DESCRIPTION OF THE INVENTION

Figure 1:
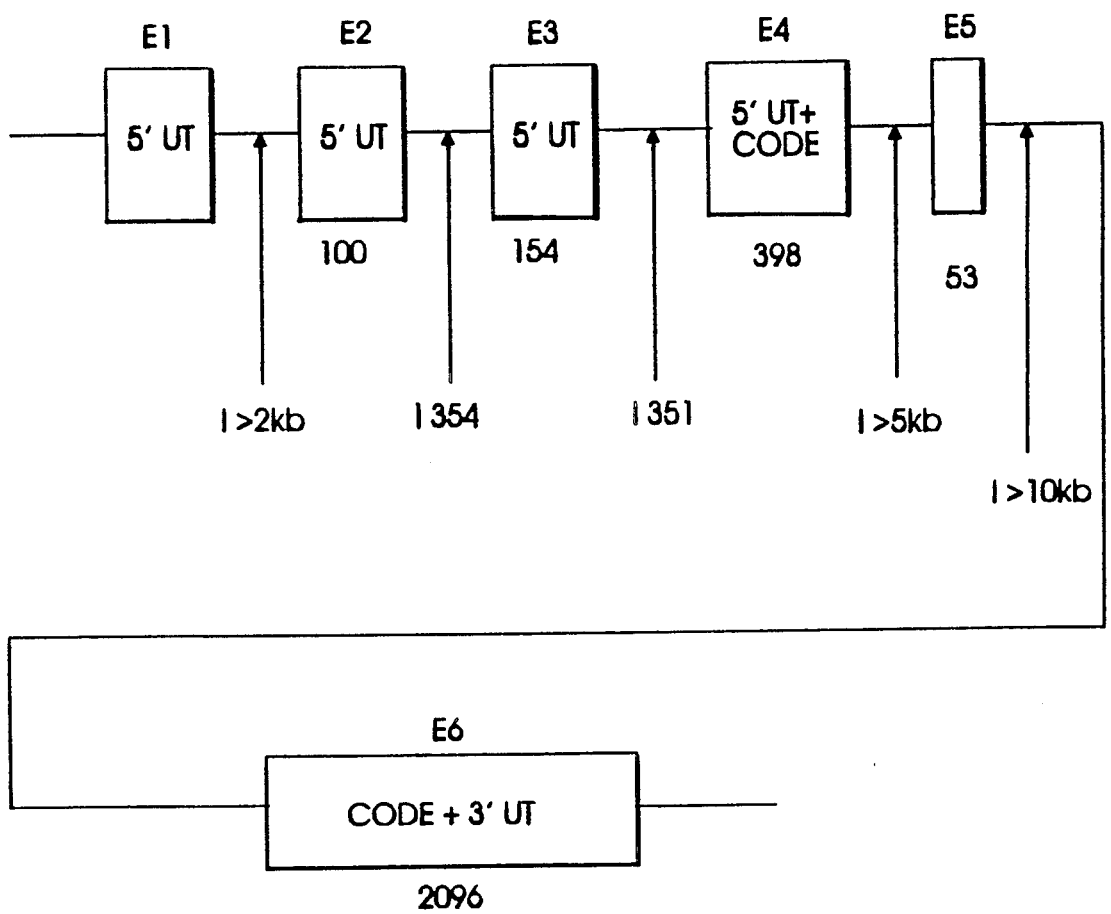
FIG. 1 provides a schematic representation of the human $A_1$ adenosine receptor gene. Shown are the known structures of the exons indicated by E1, E2, etc., and the introns indicated by capital I. Each exon displays the type of coding structure contained within its domain. For example, E1, E2 and E3 solely code for 5' untranslated regions of the messenger RNA. E4 codes for part of the 5' untranslated and the initial coding sequence of the receptor. E5 codes for a short stretch of coding region and E6 codes from the fourth transmembrane domain to the end of the coding sequence as well as the 3' untranslated region. Introns range in size from 300 b to greater than 10 kb.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., PatentIn User Manual, 99-102 (Nov. 1990)(U.S. Patent and Trademark Office, Office of the Assistant Commissioner for Patents, Washington, D.C. 20231); U.S. Pat. No. 4,871,670 to Hudson et al. at Col. 3 lines 20-43 (applicants specifically intend that the disclosure of this and all other patent references cited herein be incorporated herein by reference).

A. DNAs ENCODING $A_1$-ADENOSINE RECEPTORS AND OLIGONUCLEOTIDES THEREOF

DNAs which encode $A_1$-adenosine receptors, whether they are cDNAs or intron-containing genomic DNAs, encode a protein which, on expression in a suitable host cell, (a) selectively and stereospecifically binds adenosine, and (b) inhibits adenylate cyclase activity upon binding adenosine. This definition is intended to encompass natural allelic variations in the DNAs. Genomic DNAs of the present invention may code for an $A_1$-adenosine receptor of any species of origin, including mouse, rat, rabbit, cat, porcine, and human, but preferably code for an $A_1$-adenosine receptor of mammalian origin, and most preferably code for a human $A_1$-adenosine receptor. Complementary DNAs of the present invention encode human $A_1$adenosine receptors. Hybridization conditions which will permit other DNA sequences which code on expression for an $A_1$-adenosine receptor to hybridize to a DNA sequence as given herein are, in general, high stringency conditions. For example, hybridization of such sequences may be carried out under conditions represented by a wash stringency of 0.3M NaCl, 0.03M sodium citrate, 0.1% SDS at 60° C. or even 70° C. to DNA disclosed herein in a standard in situ hybridization assay. See J. Sambrook et al., Molecular Cloning, A Laboratory Manual (2d Ed. 1989)(Cold Spring Harbor Laboratory)). The same hybridization conditions are used to determine hybridization of oligonucleotides. In general, genomic DNA sequences which code for $A_1$-adenosine receptors and hybridize to the genomic DNA sequence encoding the human $A_1$-adenosine receptor disclosed herein will be at least 65%, 70%, 75%, 80%, 85%, 90%, or even 95% homologous or more with the sequence of the genomic DNA encoding the human $A_1$-adenosine receptor disclosed herein (with respect to the total genomic DNA). These same levels of homology apply to oligonucleotide probes which hybridize to the introns of the genomic DNA sequences disclosed herein. Homology among the exons alone between various human genomic DNA sequences encoding the $A_1$ adenosine receptor are contemplated to be of the same order as given below with respect to cDNA sequences.

In general, complementary DNA sequences which encode human $A_1$-adenosine receptors which hybridize the the cDNA encoding the human $A_1$-adenosine receptor disclosed herein will be 93%, 94%, 95%, 96%, or even 97% homologous or more to the cDNA sequence encoding the human $A_1$-adenosine receptor disclosed herein. These same levels of homology apply to oligonucleotides which hybridize to the human $A_1$-adenosine receptor cDNA or gDNA disclosed herein.

Further, DNA sequences (or oligonucleotides) which code for the same $A_1$-adenosine receptor (or fragment thereof) as coded for by the foregoing sequences, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al. at Col. 2, Table 1.

B. GENETIC ENGINEERING TECHNIQUES

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

A vector is a replicable DNA construct. Vectors are used herein either to amplify DNA encoding $A_1$-adenosine receptors as given herein and/or to express DNA which encodes $A_1$-adenosine receptors as given herein. An expression vector is a replicable DNA construct in which a DNA sequence encoding an $A_1$-adenosine receptor is operably linked to suitable control sequences capable of effecting the expression of the receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing a DNA sequence as disclosed herein constructed using recombinant DNA techniques. Transformed host cells ordinarily express the receptor, but host cells transformed for purposes of cloning or amplifying the receptor DNA do not need to express the receptor.

Suitable host cells include prokaryote, yeast or higher eukaryotic cells such as mammalian cells and insect cells. Cells derived from multicellular organisms are a particularly suitable host for recombinant $A_1$-adenosine receptor synthesis, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the DNA encoding the $A_1$-adenosine receptor to be expressed and operatively associated therewith, along with a ribosome binding site, an RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV 40 or other viral (e.g. Polyoma, Adenovirus, VSV, or BPV) source, or may be provided by the host cell chromosomal replication mechanism. If the vector is integrated into the host cell chromosome, the latter is often sufficient. Rather than using vectors which contain viral origins of replication, one can transform mammalian cells by the method of cotransformation with a selectable marker and the receptor DNA. Examples of suitable selectable markers are dihydrofolate reductase (DHFR) or thymidine kinase. This method is further described in U.S. Pat. No. 4,399,216.

Other methods suitable for adaptation to the synthesis of the $A_1$-adenosine receptor in recombinant vertebrate cell culture include those described in M-J. Gething et al., *Nature* 293, 620 (1981); N. Mantei et al., *Nature* 281, 40; A. Levinson et al., EPO Application Nos. 117,060A and 117,058A.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). The promoter and Shine-Dalgarno sequence (for prokaryotic host expression) are operably linked to the DNA encoding the $A_1$-adenosine receptor, i.e., they are positioned so as to promote transcription of $A_1$-adenosine receptor messenger RNA from the DNA.

Eukaryotic microbes such as yeast cultures may also be transformed with vectors carrying the isolated DNA's disclosed herein. see, e.g., U.S. Pat. No. 4,745,057. Saccharomyces cerevisiae is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the receptor as given herein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)). Suitable vectors and promoters for use in yeast expression are further described in R. Hitzeman et al., EPO Publn. No. 73,657.

C. USES OF GENOMIC AND COMPLEMENTARY DNAS ENCODING $A_1$-ADENOSINE RECEPTORS

1. In general. $A_1$-adenosine receptors made from cloned genes in accordance with the present invention may be used for screening compounds for $A_1$-adenosine receptor activity, or for determining the amount of a adenosine receptor agonist or antagonist in a solution (e.g., blood plasma or serum). For example, host cells may be transformed with a vector of the present invention, $A_1$-adenosine receptors expressed in that host, the cells lysed, and the membranes from those cells used to screen compounds for $A_1$-adenosine receptor binding activity. Competitive binding assays in which such procedures may be carried out are well known. By selection of host cells which do not ordinarily express an adenosine receptor, preparations free of other receptors which might interfere with the assay, such as $A_2$-adenosine receptors, can be obtained. Further, $A_1$-adenosine receptor agonists and antagonists can be identified by transforming host cells with vectors of the present invention, which host cells also express adenylyl cyclase. Membranes obtained from such cells can be used in binding studies wherein the activity of the adenylyl cyclase is monitored. $A_1$-adenosine receptor agonists will inhibit the adenylyl cyclase. Such cells must be capable of operatively associating the $A_1$-adenosine receptor with the adenylyl cyclase, i.e., G protein must also be present in the cell membranes in the appropriate configuration. Thus, a further aspect of the present invention is an aqueous solution containing cell membranes, the cell membranes containing an adenosine receptor and adenylyl cyclase, wherein the cell membranes are essentially free of $A_2$-adenosine receptors, and wherein the $A_1$-adenosine receptors are capable of inhibiting the adenylyl cyclase on binding an $A_1$-adenosine receptor agonist. A still further aspect of the present invention is an assay procedure comprising the steps of: (a) providing an aqueous solution containing cell membranes as described above; then (b) adding a test compound to the aqueous solution; and then (c) monitoring the activity of adenylyl cyclase in the aqueous solution.

DNAs of the present invention are useful in gene therapy, as discussed in greater detail below. For such purposes, retroviral vectors as described in U.S. Pat. No. 4,650,764 to Temin and Watanabe or U.S. Pat. No. 4,861,719 to Miller may be employed. DNAs of the present invention, or fragments thereof, may also be used in gene therapy carried out by homologous recombination or site-directed mutagenesis. See generally Thomas, K. and Capecchi, M., *Cell* 51, 503–512 (1987); Bertling, W., *Bioscience Reports* 7, 107–112 (1987); Smithies, O. et al., *Nature* 317, 230–234 (1985).

2. Regulation of blood vessel tone and modulation of restenosis following vessel manipulation. Adenosine receptors both $A_1$ and $A_2$ subtypes are known to exist on both vascular smooth muscle cells and endothelial cells (Mol. Pharmacol. 37:149, 1990). These receptors are known to produce vasodilatation through activation of both adenylyl cyclase (cAMP) and guanylate cyclase (cGMP) (Physiol. Rev. 70:761, 1990). The endogenous substance adenosine is responsible for producing vasodilatation in all vascular beds except renal and perhaps pulmonary, where constriction occurs (Physiol. Rev. 70:761, 1990; Circ. 65:1516, 1989). In addition, vascular constriction can be overcome by adenosine's action. Recombinant DNA constructs such as the vectors described herein can be introduced into the blood vessel via catheter based techniques (Circ. 83:2007, 1991) to permit the transfection of the vessel with exogenous gene products to overexpress or inhibit the activity of the $A_1$ adenosine receptor.

Thus, a further aspect of the present invention is a method of treating a human or animal (e.g., horse, cow) subject by administering a vector carrying a DNA sequence or oligonucleotide or fragment thereof as described herein into a blood vessel of the subject (i.e., artery, vein) in an amount sufficient so that (depending on the nature of the vector and the specific purpose as discussed below) expression of the $A_1$ adenosine receptor is increased or inhibited.

For example, a restriction fragment of the human $A_1AR$ cDNA could be inserted into pCMV or retroviral vectors. Retroviral vectors have certain advantages in that they have high efficiency for transfection and are effective in a wide range of cell types. The disadvantages are their potential for inducing malignant transformation or producing a competent virus and hence produce an infection. These techniques are discussed in Wilson et al., *Human Gene Therapy* 3, 179 (1991), which describes the transformation of human liver cells deficient in LDL receptors with DNA encoding LDL receptors using retroviral vectors. Similar approaches with DNAs encoding adenosine receptors could be accomplished.

A specific example is as follows. A cDNA as given herein is cloned into the MuLV vector which is a MO-MuLV derived vector containing Ψ packaging sequences, transposon TN5 gene which encodes neomycin phosphotransferase, SV40 origin of replication, pBR origin of replication: beta actin promoter and unique Bam H1 cloning site. Once constructed the plasmids are isolated, purified and analyzed by restriction digestion using standard procedures.

Plasmid constructs are transfected with 3T3Ψ2 packaging cell line and media from these cells can be used to infect the 3T3ΨAM packaging cell line. G418 resistent clones of 3T3ΨAM cells are isolated and used as a source of retroviruses for infecting target cells (*J. Virol.* 31:360, 1990; *Cell* 33:153, 1983; *Proc. Natl. Acad. Sci.* 31:6349, 1984). This technique could of course be modified in a number of ways. For example, the more recently described ΨCRIP packaging cell line could also be utilized (*Proc. Natl. Acad. Sci. USA* 85:6460, 1988). Once the vectors are made they can be mixed with a lipofectin mixture as described (Circ. 83:2007, 1991) and then introduced in a blood vessel using a perfusion balloon catheter in accordance with known techniques. Recent data suggest that lipofectin may not be necessary. In this manner $A_1AR$ can be overexpressed to enhance the activity of $A_1AR$ to module vascular tone/growth properties. Similar receptors in which sites for phosphorylation (*J. Biol. Chem.* 264:12657, 1989; *Mol. Pharmacol.* 40:639, 1991), which lead to desensitization of the receptor, are mutated out could be introduced to thwart the process of desensitization. Although two expression vectors are described above, the $A_1AR$ could also be expressed using a wide range of expression vectors including those with regulatable promoters either with heavy metal promoters or glucocorticoid promoters, etc. In addition, transfection systems utilizing site specific cogeners, such as antibody/-lipid mixtures or DNA constructs attached to antibodys for targeting, could also be used.

The receptors to be transfected into vessels would not be limited to wild type human $A_1AR$ but mutants which are constitutively active or inactive, receptors which couple to G protein other than $G_i$ (such as $G_s$ or $G_o$) constructed by interchanging the third cytoplasmic loop from receptors such as the $\beta$-adrenergic or $A_2$ adenosine receptors which couple to $G_s$ for the third cytoplasmic loop of $A_1AR$.

In addition, one can express antisense RNA from the human $A_1$-adenosine receptor DNAs disclosed herein to block production of the $A_1AR$, particularly antisense RNA directed to one of the intron-exon junctions of the genomic $A_1$ sequence.

Another potential use is to introduce these wild type or mutant receptors at the time of coronary angioplasty to modulate the vessels' reactivity at the site of balloon injury. These transfections could be used to promote enhanced vasodilation or to change the growth properties of the endothelial cells or smooth muscle cells. Further, adenosine has been reported to enhance collateral formation and angiogenesis. Thus, by introducing receptor constructs one could modulate growth of vessels in the heart or other organs.

3. Cardio-protective effects. As described above, there is now evidence that protection against myocardial infarction afforded by the preconditioning, i.e., short-term occlusion of a coronary artery is mediated by $A_1$ adenosine receptors (*Circ.* 84:350, 1991). It appears that activation of the $A_1$ adenosine receptor by adenosine during a brief ischemic event by some mechanism as yet unclear protects the heart to subsequent ischemic and anoxic conditions. Therefore, enhancement of the effects of $A_1$ adenosine receptors may lead to greater protection of the myocardium to ischemia. This would have direct impact during procedures such as coronary artery bypass grafting, during coronary angioplasty, or in patients at high risk for myocardial infarction.

Thus, an additional aspect of the present invention is a method of combatting ischemia in a human or animal subject in need of such treatment, comprising administering to the subject (e.g., intraveneously) a vector carrying a DNA as given herein, and capable of expressing the same in myocardial tissue, in an amount effective to combat ischemia in said subject.

There are several approaches that could be taken to implement enhanced $A_1$ receptor function. One would be to over-express wild type human $A_1$ receptors in the myocardium so that, for a given level of adenosine present extracellularly, there would e an enhanced signal through the G-protein mechanism to create an enhanced protective effects. This could be accomplished by inserting the cDNA fragments, as described above, into an expression vector which could be targeted for myocardial cells based on specific antigens on the surface of cardiac cells. A second approach is that, by understanding the promoter/enhancer region of the gene, one can specifically target means of activating a promoter/enhancer region to increase the transcription and ultimately translation of the messenger RNA for the $A_1$ receptor to enhance the relative levels of $A_1$ receptors in the heart. Multiple approaches are currently being studied worldwide (*Trends in Cardio. Med.* 7:271, 1991).

4. Control of arrhythmias. Adenosine has been found to be a very effective antiarrhythmic agent for supraventricular tachycardias (*Circ.* 83:1499, 1991). The effects are known to occur through its action on $A_1$ adenosine receptors on the SA node and the AV node. The arteries subserving these regions of the heart are now accessible through cardiac catheterization techniques and, therefore, direct access to these areas can be obtained with the potential for delivering specific vectors containing cDNA sequences of the $A_1$ adenosine receptor. There are at least two potential uses, one for the treatment of supraventricular tachycardias in which additional wild-type $A_1$ receptors could be delivered to either the AV node or the SA node, thereby increasing the effectiveness of endogenous adenosine on slowing the SA and AV node. Another potential treatment is for bradyarrthythmias in which there is excessive slowing of the SA and AV node, in which case antisense RNA could be expressed in this region by the introduction of a vector carrying the appropriate cDNA to block the production of the $A_1$ receptor in these areas, thus diminishing the effect of endogenous adenosine on heart rate and allowing an increased heart rate to occur. For all the above applications, one would utilize transient transfections likely working through an episomal mode since these cells do not replicate and, therefore, stable transfections are not likely to occur.

5. CNS therapies. The same type of protective effect as described in the heart may well also occur in the brain during strokes. Therefore, there is the potential for delivering the same type of constructs described for the cardioprotective effect above into regions of the brain subject to ischemia.

6. Treatment of cystic fibrosis. There has been recent evidence published whereby blockade of the $A_1$ adenosine receptors from cystic fibrosis cells activates chloride efflux from these cells. This work was able to document that the $A_1$ adenosine receptor antagonist known as cyclopentyl-1,3-dipropylxanthine activated chloride efflux from a cell line derived from cystic fibrosis patients which is known to contain mutant phenylalanine 508 characteristic of cystic fibrosis. There would be several potential mechanisms for blocking the effects of endogenous adenosine in these cells. First, one could transfect into these cells DNA encoding a human $A_1$-adenosine receptor which would bind adenosine but would not activate the effector system. Examples of these approaches include the construction of an adenovirus vector which is a replication deficient recombinant adenovirus such as the Ad-CITR construct used in cystic fibrosis. This is constructed from the adenovirus type 5 (Ad5) deletion mutant, Ad-d1324 and a plasmid (pTG 595T) as described (*Cell* 68:143, 1992) This or other vectors could be delivered in an aerosolized form in lipid or saline or could be introduced with cell specificity using an ectopic murine retrovirus to infect only the chosen cell through antibody mediated binding of a cell surface receptor. Alternatively, polycations such as poly-L-lysine to encapsalate and deliver the construct to the cell surface (*Thorax.* 46:46, 1991) thus creating a receptor which was constituently blocked. Another mechanism would be to use antisense approaches to block synthesis of the receptor as described above. Additionally, one could use pharmacological methods (covalent ligands) to block receptors with agents that would specifically bind to the receptor and covalently inhibit its activity.

7. Ocular uses of DNA encoding A:AR. Recent information (*Current Eye Research* 11:453, 1992) demonstrates that R-PIA (an $A_1$AR selective ligand) at selective doses when applied to the eye of rabbits leads to a significant reduction in intraocular pressure (5-8 mmHg) and this response is blocked by adenosine receptor antagonist. These data open the way for introducing constitutively active $A_1$AR, $A_1$AR resistent to desensitization or over expression of wild type $A_1$AR into interior chamber structures such as the ciliary body, muscles, etc., in order to enhance $A_1$AR efforts and lower extraocular pressure. The same type of vectors and constructs as described above could be used here. Likely the constructs would need to be injected for delivery.

8. Antisense oligonucleotides. Another aspect of this invention is an antisense oligonucleotide having a sequence capable of binding specifically with any sequences of an mRNA molecule which encodes a human $A_1$ adenosine receptor so as to prevent translation of the mRNA molecule (binding conditions may be at the stringencies as given above with respect to DNA hybridization). The antisense oligonucleotide may have a sequence capable of binding specifically with any sequences of the DNA molecule whose sequence is disclosed herein in SEQ ID NO:1, SEQ ID NO:3, SEQ ID NO:5. Chemical analogs of nucleotides (e.g., nucleotides in which the phosphodiester bonds have been modified, e.g., to the methylphosphonate, the phosphotriester, the phosphorothioate, the phosphorodithioate, or the phosphoramidate, so as to render the oligonucleotide more stable in vivo) are specific examples of such antisense oligonucleotides. Antisense oligonucleotides may be of any suitable length (e.g., from about 10 to 60 nucleotides in length), depending on the particular target being bound and the mode of delivery thereof. Preferably the antisense oligonucleotide is directed to an mRNA region containing a junction between intron and exon. Where the antisense oligonucleotide is directed to an intron/exon junction, it may either entirely overlie the junction or may be sufficiently close to the junction to inhibit splicing out of the intervening exon during processing of precursor mRNA to mature mRNA (e.g., with the 3' or 5' terminus of the antisense oligonucleotide being is positioned within about, for example, 10, 5, 3, or 2 nucleotides of the intron/exon junction).

Pharmaceutical compositions comprising an antisense oligonucleotide as given above effective to reduce expression of a human $A_1$ adenosine receptor by passing through a cell membrane and binding specifically with mRNA encoding a human $A_1$ adenosine receptor in the cell so as to prevent its translation are another aspect of the present invention. Such compositions are provided in a suitable pharmaceutically acceptable carrier (e.g., sterile pyrogen-free saline solution). The antisense oligonucleotides may be formulated with a hydrophobic carrier capable of passing through a cell membrane (e.g., in a liposome, with the liposomes carried in a pharmaceutically acceptable aqueous carrier). The oligonucleotides may also be coupled to a substance which inactivates mRNA, such as a ribozyme. Such oligonucleotides may be administered to a subject to inhibit the activation of $A_1$ adenosine receptors, which subject is in need of such treatment for any of the reasons discussed herein.

9. Additional uses. DNAs of the present invention, and oligonucleotides derived therefrom, are useful for screening for restriction fragment length polymorphism (RFLP) associated with disorders such as cystic fibrosis or other disorders potentially involving a defective $A_1$-adenosine receptor (or defective regulation thereof).

Oligonucleotides of the present invention are useful as diagnostic tools for probing $A_1$-adenosine receptor expression in various tissues. For example, tissue can be probed in situ with oligonucleotide probes carrying detectable groups (e.g., a radioisotope such as $^{32}P$, $^{125}I$, $^{131}I$, $^3H$, $^{14}C$, or $^{35}S$; an enzyme such as horseradish peroxidase, or alkaline phosphatase; an electron dense ligand such as ferritin or gold) by conventional autoradiography techniques to investigate native expression of this receptor or pathological conditions relating thereto. Further, chromosomes can be probed to investigate the presence or absence of an $A_1$-adenosine receptor gene, and potential pathological conditions related thereto.

The present invention is explained in greater detail in the following Examples. These Examples are for illustrative purposes only, and are not to be taken as limiting of the invention.

EXAMPLES

I. Methods

[g$^{32}$P]ATP, [$^{35}$S]dATP, [a$^{32}$P]ATP and [$^3$H]HAX were from DuPont-New England Nuclear. Restriction enzymes and T4 DNA ligase were from either Boehringer-Mannheim or Promega. The pCMV5 expression vector was obtained from Dr. Marc Caron (Duke University Medical Center) and was originally described by Dr. David Russell (University of Texas). All cell culture supplies were from Gibco.

Genomic Cloning. The human $A_1$ adenosine receptor ($A_1$AR) genomic clones were isolated from human leukocyte genomic library (Clonetech) in EMBL3 with various probes. In general, each time $\sim 1.0 \times 10^6$ plaques were screened. Duplicate nylon filters (Biotrans, ICN)

with lifted plaques were prehybridized in 50% formamide (30% with shorter probe), 5x SSPE (1x SSPE=0.15M NaCl, 0.01M Na$_2$HPO$_4$ and 1 mM EDTA, pH 7.4), 5x Denhardt's solution, 0.1% SDS and 0.1 mg/ml salmon sperm DNA for 4 hrs at 42° C.. Hybridization was conducted in the same solution without Denhardt's solution, plus radiolabeled probe (~500,000 cpm/mo) for about 16 hrs at 42° C.. The filters were then washed twice in 2x SSC (1x SSC=0.15M NaCl and 0.015M sodium citrate) and 0.1% SDS at room temperature for 15 min each. The final wash conditions were determined according to the length of probe used for screening, ranging from 1 x SSC, 0.1% SDS, 55° C. and 10 min to 0.1x SSC, 0.1% SDS, 60° C. and 10 min.

The structure of the human genomic adenosine A$_1$ receptor gene is set forth in SEQ ID NO:1 and SEQ ID NO:3, with the amino acid fragment coded in SEQ ID NO:1 set forth in SEQ ID NO:2, and with the amino acid fragment coded in SEQ ID NO:3 set forth in SEQ ID NO:4. Note that SEQ ID NO:1 contains part of intron 1, all of exon 2, all of intron 3, all of exon 4, and part of intron 4, while SEQ ID NO: 3 contains part of intron 5, and all of exon 6. Portions not shown can be derived from the portions shown by standard techniques such as polymerase chain reaction (PCR) or other of the known amplification techniques, taken with the information provided in all of the sequences herein. For example, it can be determined from these materials that exon number 5 contains nucleotides 752 to 804 of SEQ ID NO:5, and the introns immediately flanking exon number 5 can be produced in full in a routine manner with amplification primers taken from exon number 5 and the flanking sequence information disclosed herein.

The information set forth in SEQ ID NO:1 and SEQ ID NO:3 was obtained as follows:

The first genomic clone "D" which contains exon 6, the longest exon, was isolated with the full length bovine A$_1$ adenosine receptor cDNA as a probe. See GenBank TM/EMBL Data Bank Accesion Number M86261; M. Olah et al., supra. A KpnI fragment of the genomic clone was subcloned into pGEM4Z (Promega) and sequenced with Sequenase version 2 DNA sequencing kit (United States Biochemical).

The second genomic clone "B" which contains exon 2-4 was isolated with a PCR fragment (based on bovine A$_1$AR cDNA sequence 526-854) as a probe. An EcoRI fragment (~7 kb) from the genomic clone restriction digest was subcloned and sequenced.

The genomic clone "A" which contains exon 1 was isolated with the EcoRI/NheI fragment (~110 bp) of human A$_1$AR cDNA clone 7A (see below) as a probe. A SphI fragment of this clone was subcloned.

The genomic clone "C" which contains exon 5 was isolated with a 50 mer synthetic oligonucleotide (based on human A$_1$AR cDNA sequence 755-804) as a probe. A KpnI fragment from this clone was subcloned.

cDNA Cloning. Human A$_1$AR cDNA clones were isolated from human brain (hippocampus) cDNA library in lambda ZAP II (Stratagene) with the SalI/HindIII fragment of the subclone of genomic clone "D" as a probe. The conditions used for library screening were the same as that used for genomic library screening. From ~1.0×10$^6$ plaques, 56 positive clones were identified. Among nine analyzed clones, two containing longest inserts, 6A (2.61 kb) and 7A (2.48 kb), were sequenced. Clone 6A has a short 5'-untranslated sequence (120 bp), a full coding region (981 bp) and a complete 3'-untranslated sequence with polyadenylation signal and a poly (A) tail (1.51 kb). Clone 7A has a 410 bp 5'-untranslated sequence but missing a part of 3' sequence (1.09 kb rather than 1.51 kb). A more complete cDNA sequence of 2.9 kb, given herein as SEQ ID NO:5, is deduced from the combination of 6A (291-2900) and 7A (1-2480) sequences. The amino acid sequence coded for by the cDNA of SEQ ID NO:5 is set forth in SEQ ID NO:6.

Expression Vector Construction. An EcoRI/XbaI fragment of the human A$_1$AR cDNA clone 6A (291-1630) was subcloned into the pCMV5 expression vector in accordance with known techniques. See, e.g., M. Olah et al., *J. Biol. Chem.* 267, 10764-10770 (1992).

II. Results

Screening of the human genomic library revealed multiple positive clones. Subcloning and sequencing of a number of these positive clones revealed that the human gene contained intronic interruptions of coding sequence based on the homology predicted from the known sequence of the bovine A$_1$ adenosine receptor cDNA. See M. Olah et al., *J. Biol. Chem.* 267, 10764-10770 (1992). Thus, unlike most G-protein coupled seven transmembrane domain receptors, the gene for the human A$_1$ adenosine receptor is not an intronless gene, but as can be seen in the schematic in FIG. 1 (T. Bonner et al., *Science* 237, 527-532 (1987)) there are six exons interrupted by introns of various sizes. The full sequence of the exon structure and partial sequence of the intron structures are demonstrated in SEQ ID NO:1 and SEQ ID NO:3.

Figure 2:
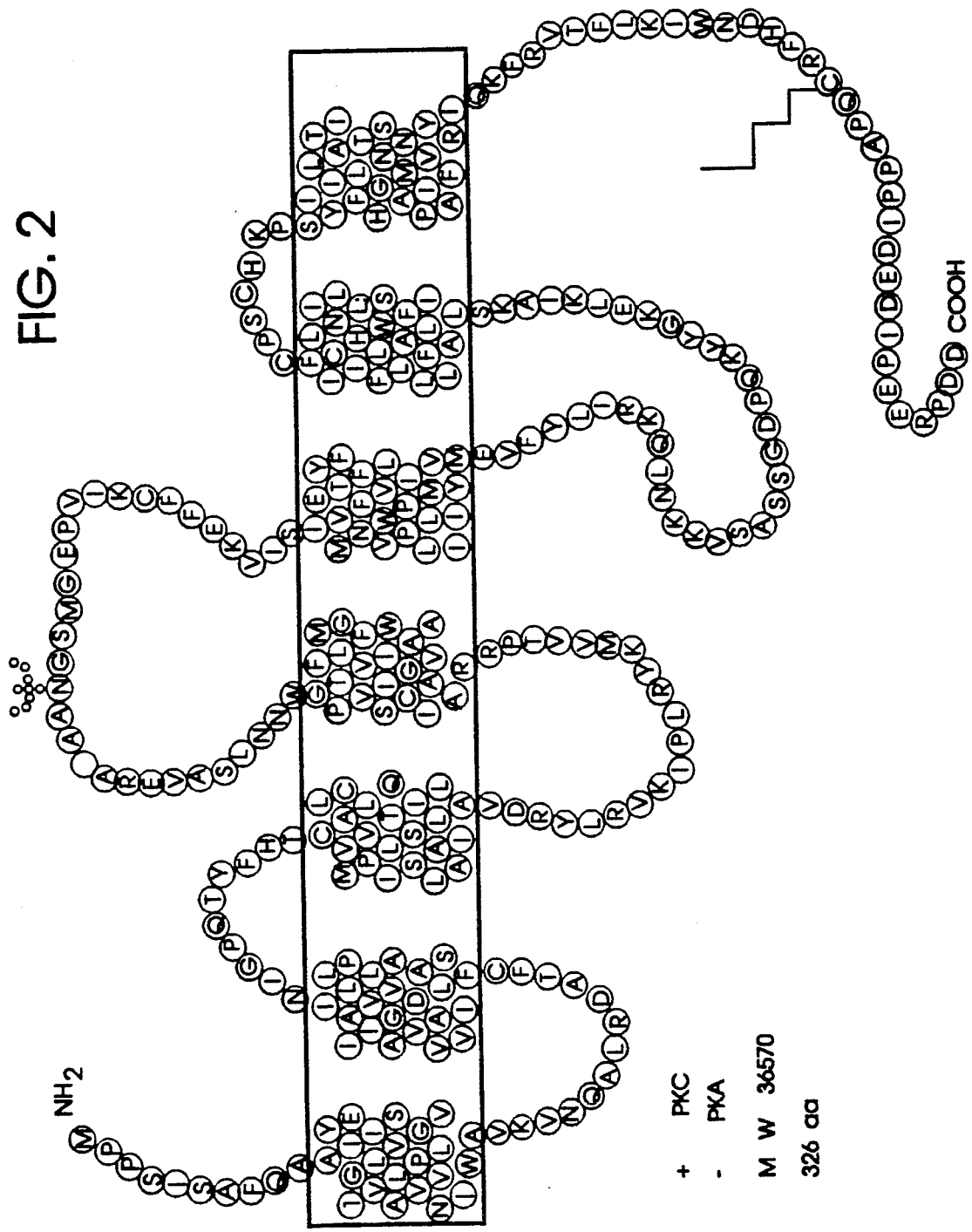
FIG. 2 shows the predicted structure of the human $A_1$ adenosine receptor as predicted by hydropathy plots. Demonstrated are the potential phosphorylation sites for protein kinase C and protein kinase A. In addition, potential glycosylation sites are shown by the asterisk or the small "fork-like" structure demonstrated coming off the second extracellular loop at the top of the figure. In addition are shown the potential site for fatty acid acylation on the carboxy terminal tail.

We next identified a human A$_1$ receptor cDNA by isolating a fragment from a human brain cDNA library. Two almost full length cDNAs were isolated. Clone 6A contains a short 5' untranslated sequence, followed by a full coding sequence and the complete 3' untranslated sequence with a polyadenylation signal and a poly-A tail. Clone 7A has a 400-base pair 5' untranslated region but is missing a part of the 3' sequence as defined from the 6A clone. Thus, a more complete cDNA sequence can be deduced from a combination of the 6A and 7A sequences as given in SEQ ID NO:5. A direct comparison of the translated cDNAs from the bovine, dog, rat and human A$_1$ adenosine receptors (data not shown) indicates homology in the range of 90% between all the A$_1$ receptors. It should be noted that these sequence differences are important as can be verified by the fact that each receptor has a different pharmacology. See M. Olah et al., supra. An EcoRI/XbaI restriction fragment from the cDNA has been subcloned into the PCMV-5 expression vector as described in M. Olah et al., supra, and studies are currently underway expressing this receptor. A predicted structure for the human A$_1$AR is shown in FIG. 2.

Mutagenesis studies carried out in the bovine A$_1$ adenosine receptor have revealed that mutation of Hist-278 to Leu-278 (found in transmembrane domain 7) dramatically decreases both agonist and antagonist binding by >90%. This confirms previous biochemical data suggesting that histine residues are important for the binding of adenosine and its analogues to this receptor. In contrast, mutation of Hist-251 in transmembrane domain 6 to Leu-251 decreased antagonist affinity by four fold but had no effect on the affinity of agonists for the receptor. See M. Olah et al., supra. This suggests that one can manipulate the receptor in a way to alter how agonists and antagonists bind to the receptor, thereby providing potential therapeutic implications as described herein.

Mutations of phenylalanines 185 and 186 residues to leucines 185 and 186 in transmembrane domain-5 of the receptor results in a mutant receptor which binds agonists with high affinity, indicating that the coupling of the receptor to its G-protein is normal, but these receptors fail to inhibit adenylyl cyclase in transfected CHO cells. This work was performed using the bovine $A_1AR$ but the human $A_1AR$ is identical in the region mutated (the hydrophobic pocket in the fifth transmembrane domain). This provides further evidence that the receptors can be manipulated to make the receptor become essentially an antagonist receptor in that it will bind agonist with full high affinity but is incapable of activating or inhibiting an effector. While receptor DNAs mutated in this manner are preferably human, they could be of other species (e.g., bovine, rat). These also has therapeutic potentials as described herein.

The foregoing examples are illustrative of the present invention, and are not to be construed as limiting thereof. The invention is defined by the following claims, with equivalents of the claims to be included therein.

---

That which is claimed is:

1. Isolated DNA encoding an $A_1$ adenosine receptor selected from the group consisting of:
   (a) isolated human genomic DNA which encodes the human $A_1$ adenosine receptor given herein as SEQ ID NO:6 and which contains the DNA sequences given herein as SEQ ID NO:1 and SEQ ID NO:3;
   (b) isolated human genomic DNA which hybridizes to isolated DNA of (a) above under conditions represented by a wash stringency of 0.3M NaCl, 0.03M sodium citrate, and 0.1% SDS at 60° C., and which encodes a human $A_1$ adenosine receptor; and
   (c) isolated DNA differing from the isolated DNAs of (a) and (b) above in nucleotide sequence due to the degeneracy of the genetic code, and which encodes an $A_1$ adenosine receptor encoded by isolated DNA of (a) or (b) above.

2. A recombinant DNA comprising vector DNA and a DNA according to claim 1.

3. A recombinant DNA according to claim 2, wherein said vector DNA comprises a vector selected from the group consisting of plasmids, adenoviruses, and cytomegaloviruses.

4. A recombinant DNA according to claim 2, wherein said vector DNA comprises a baculovirus vector.

5. A host cell containing a recombinant DNA of claim 2 and capable of expressing the encoded protein.

6. A host cell according to claim 5, wherein said host cell is a mammalian cell.

7. A host cell according to claim 5, wherein said host cell is selected from the group consisting of baby hamster kidney cells, mouse cells, human embryo cells, and chinese hamster ovary cells.

8. A host cell according to claim 5, wherein said host cell is an insect cell.

9. Isolated DNA encoding an $A_1$ adenosine receptor selected from the group consisting of:
   (a) isolated DNA which encodes a human $A_1$ adenosine receptor comprising DNA having the sequence given herein as SEQ ID NO:5;
   (b) isolated DNA which hybridizes to isolated DNA of (a) above under conditions represented by a wash stringency of 0.3M NaCl, 0.03M sodium citrate, and 0.1% SDS at 60° C., and which encodes a human $A_1$ adenosine receptor; and
   (c) isolated DNA differing from the isolated DNAs of (a) and (b) above in nucleotide sequence due to the degeneracy of the genetic code, and which encodes a human $A_1$ adenosine receptor encoded by isolated DNA of (a) or (b) above.

10. A recombinant DNA comprising vector DNA and a DNA according to claim 9.

11. A recombinant DNA according to claim 10, wherein said vector DNA comprises a vector selected from the group consisting of plasmids, adenoviruses, and cytomegaloviruses.

12. A recombinant DNA according to claim 10, wherein said vector DNA comprises a baculovirus vector.

13. A host cell containing a recombinant DNA of claim 10 and capable of expressing the encoded protein.

14. A host cell according to claim 13, wherein said host cell is a mammalian cell.

15. A host cell according to claim 13, wherein said host cell is selected from the group consisting of baby hamster kidney cells, mouse cells, human embryo cells, and chinese hamster ovary cells.

16. A host cell according to claim 13, wherein said host cell is an insect cell.

17. An oligonucleotide capable of binding to an intron of the $A_1$ adenosine receptor gene, said oligonucleotide selected from the group consisting of:
   (a) (i) isolated DNA comprising the first intron of the human genomic DNA encoding the human $A_1$ adenosine receptor according to SEQ ID NO:6, (ii) isolated DNA comprising the second intron of the human genomic DNA encoding the human $A_1$ adenosine receptor according to SEQ ID NO:6, (iii) isolated DNA comprising the third intron of the human genomic DNA encoding the human $A_1$ adenosine receptor according to SEQ ID NO:6, (iv) isolated DNA comprising the fourth intron of the human genomic DNA encoding the human $A_1$ adenosine receptor according to SEQ ID NO:6, and (v) isolated DNA comprising the fifth intron of the human genomic DNA encoding the human $A_1$ adenosine receptor according to SEQ ID NO:6; and
   (b) isolated DNA which hybridizes to the isolated DNAs of (a) above under conditions represented by a wash stringency of 0.3M NaCl, 0.03M sodium citrate, and 0.1% SDS at 60° C.

18. An oligonucleotide according to claim 17 labelled with a detectable group.

19. A recombinant DNA comprising vector DNA and an oligonucleotide according to claim 17.

20. A recombinant DNA according to claim 19, wherein said DNA is capable of exchanging said oligonucleotide with a homologous nucleotide in a suitable cell by homologous recombination.

21. Isolated human genomic DNA which encodes the human $A_1$ adenosine receptor given herein as SEQ ID NO:6 and which contains the DNA sequences given herein as SEQ ID NO:1 and SEQ ID NO;3.

22. A recombinant DNA comprising vector DNA and DNA according to claim 21.

23. A recombinant DNA according to claim 22, wherein said vector DNA comprises a vector selected from the group consisting of plasmids, adenoviruses, and cytomegaloviruses.

24. A recombinant DNA according to claim 22, wherein said vector DNA comprises a baculovirus vector.

25. A host cell containing a recombinant DNA of claim 22 and capable of expressing the encoded protein.

26. Isolated DNA which encodes a human $A_1$ adenosine receptor having the sequence given herein as SEQ ID NO:5.

27. A recombinant DNA comprising vector DNA and a DNA according to claim 26.

28. A recombinant DNA according to claim 27, wherein said vector DNA comprises a vector selected from the group consisting of plasmids, adenoviruses, and cytomegaloviruses.

29. A recombinant DNA according to claim 27, wherein said vector DNA comprises a baculovirus vector.

30. A host cell containing a recombinant DNA of claim 27 and capable of expressing the encoded protein.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
       ( A ) LENGTH: 1513 base pairs
       ( B ) TYPE: nucleic acid
       ( C ) STRANDEDNESS: single
       ( D ) TOPOLOGY: linear ( i i ) MOLECULE TYPE: DNA (genomic)

( i x ) FEATURE:
       ( A ) NAME/KEY: intron
       ( B ) LOCATION: 1..71

( i x ) FEATURE:
       ( A ) NAME/KEY: exon
       ( B ) LOCATION: 72..161

( i x ) FEATURE:
       ( A ) NAME/KEY: intron
       ( B ) LOCATION: 162..525

( i x ) FEATURE:
       ( A ) NAME/KEY: exon
       ( B ) LOCATION: 526..679

( i x ) FEATURE:
       ( A ) NAME/KEY: intron
       ( B ) LOCATION: 680..1030

( i x ) FEATURE:
       ( A ) NAME/KEY: exon
       ( B ) LOCATION: 1031..1428

( i x ) FEATURE:
       ( A ) NAME/KEY: CDS
       ( B ) LOCATION: 1088..1426

( x i ) SEQUENCE DESCRIPTION: SEQ ID NO:1:

| | | | | | | |
|---|---|---|---|---|---|---|
| CAGGCGCCCG | AGTCGAGTCC | CAGCCAGCTA | CCATCCCTCT | GGAGCTTACC | GGCCGGCCTT | 60 |
| GGCTTCCCCA | GGAATCCCTG | GAGCTAGCGG | CTGCTGAAGG | CGTCGAGGTG | TGGGGGCACT | 120 |
| TGGACAGAAC | AGTCAGGCAG | CCGGGAGCTC | TGCCAGCTTT | GGTGACCTTG | GGTAAGTCTG | 180 |
| AGTCTCGGTT | CACCCCTGGG | GCTCCCCAAT | GGGGGTGCAG | GAGAGGGTTG | AAAGAAGAGA | 240 |
| CCGGAATGGC | CCCTTGGGGC | AGGCCATGGG | CAAGGTTCCC | CGACAGAGCT | GGAACGGGAC | 300 |
| CAGAGGACTG | CTAAGATCCA | GGCACCAGGA | CGGGTCTCAA | GGTGGGTGGG | CGCAGGGCAG | 360 |
| GTGCGGGCAC | GCTGAGGGAA | TAGGGAGAAA | ACGCCCCAGC | CTTGTCCTGG | GCTCCGTCCC | 420 |
| CAGACCCACG | TCTGCCACCC | CAGTCCCAGG | TGCGAAACAG | GGGCGCTAC | CTCTTTAAAA | 480 |
| GCGTCCGGGG | CTGAGTCTCT | GCCGTACCAT | GTGATTGCTT | GAAAGGCCGG | GCTGGAGCG | 540 |
| CTGCGGCGGG | AGCCGGAGGA | CTATGAGCTG | CCGCGCGTTG | TCCAGAGCCC | AGCCCAGCCC | 600 |

| | | |
|---|---|---|
| TACGCGCGCG GCCCGGAGCT CTGTTCCCTG GAACTTTGGG CACTGCCTCT GGGACCCCTG | 660 |
| CCGGCCAGCA GGCAGGATGG TGAGCTCCCT GCATCCTGTT CTGTGCACAG GGGTGGGCAG | 720 |
| AGCCAGTCAT GGGAGACCCC TCTGTGCGTG TGTCTGTGTG TGCGCGCGCG CTGGGAGCTG | 780 |
| CCTCACACCT CATAAAAAAG CCAGTGGAGG AGTGAGGCTG CTATTTAAG TTGCTGAATG | 840 |
| GAACCTCTGG GAATGATAAA GGAAAGGGAC AAAGATTAGG CAGAGAAGGG TCCGGGTGCC | 900 |
| CCTCCAGCCT GGGTAGGAGC TGCATGTGAC AAGTGGGACA CATCACAGGG TACCTGGAGT | 960 |
| TCCAGGGCAG CCTGAGCTCC CTGCCCCTCC CAGACCGGTC TCCCCATCCC AGGCTTCCCT | 1020 |
| GACCACACAG GTGCTTGCCT CGTGCCCCTT GGTGCCCGTC TGCTGATGTG CCCAGCCTGT | 1080 |

```
GCCCGCC ATG CCG CCC TCC ATC TCA GCT TTC CAG GCC GCC TAC ATC GGC     1129
        Met Pro Pro Ser Ile Ser Ala Phe Gln Ala Ala Tyr Ile Gly
         1               5                  10

ATC GAG GTG CTC ATC GCC CTG GTC TCT GTG CCC GGG AAC GTG CTG GTG     1177
Ile Glu Val Leu Ile Ala Leu Val Ser Val Pro Gly Asn Val Leu Val
 15              20                  25                  30

ATC TGG GCG GTG AAG GTG AAC CAG GCG CTG CGG GAT GCC ACC TTC TGC     1225
Ile Trp Ala Val Lys Val Asn Gln Ala Leu Arg Asp Ala Thr Phe Cys
                 35                  40                  45

TTC ATC GTG TCG CTG GCG GTG GCT GAT GTG GCC GTG GGT GCC CTG GTC     1273
Phe Ile Val Ser Leu Ala Val Ala Asp Val Ala Val Gly Ala Leu Val
             50                  55                  60

ATC CCC CTC GCC ATC CTC ATC AAC ATT GGG CCA CAG ACC TAC TTC CAC     1321
Ile Pro Leu Ala Ile Leu Ile Asn Ile Gly Pro Gln Thr Tyr Phe His
         65                  70                  75

ACC TGC CTC ATG GTT GCC TGT CCG GTC CTC ATC CTC ACT CAG AGC TCC     1369
Thr Cys Leu Met Val Ala Cys Pro Val Leu Ile Leu Thr Gln Ser Ser
     80                  85                  90

ATC CTG GCC CTG CTG GCA ATT GCT GTG GAC CGC TAC CTC CGG GTC AAG     1417
Ile Leu Ala Leu Leu Ala Ile Ala Val Asp Arg Tyr Leu Arg Val Lys
 95                 100                 105                 110

ATC CCT CTC CGGTGAGTCC ACAGCCCGA AGTACTCGCA GCACCACATG              1466
Ile Pro Leu
ATGGCTGGCT TGAGGGCCAT CTAGAAAGGA AAAAAGGTAG AGCATAA                 1513
```

(2) INFORMATION FOR SEQ ID NO:2:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Pro Ser Ile Ser Ala Phe Gln Ala Ala Tyr Ile Gly Ile Glu
 1               5                  10                  15

Val Leu Ile Ala Leu Val Ser Val Pro Gly Asn Val Leu Val Ile Trp
             20                  25                  30

Ala Val Lys Val Asn Gln Ala Leu Arg Asp Ala Thr Phe Cys Phe Ile
         35                  40                  45

Val Ser Leu Ala Val Ala Asp Val Ala Val Gly Ala Leu Val Ile Pro
     50                  55                  60

Leu Ala Ile Leu Ile Asn Ile Gly Pro Gln Thr Tyr Phe His Thr Cys
 65                  70                  75                  80

Leu Met Val Ala Cys Pro Val Leu Ile Leu Thr Gln Ser Ser Ile Leu
                 85                  90                  95

Ala Leu Leu Ala Ile Ala Val Asp Arg Tyr Leu Arg Val Lys Ile Pro
            100                 105                 110
```

Leu ( 2 ) INFORMATION FOR SEQ ID NO:3:

( i ) SEQUENCE CHARACTERISTICS:
        ( A ) LENGTH: 2180 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 1..29

( i x ) FEATURE:
        ( A ) NAME/KEY: exon
        ( B ) LOCATION: 30..2125

( i x ) FEATURE:
        ( A ) NAME/KEY: CDS
        ( B ) LOCATION: 32..616

( x i ) SEQUENCE DESCRIPTION: SEQ ID NO:3:

```
TTGACCTGCA GGTCGACCTG CAGGTCAACG G ATC CTC TCC TTC GTG GTG GGA            52
                                   Ile Leu Ser Phe Val Val Gly
                                    1               5

CTG ACC CCT ATG TTT GGC TGG AAC AAT CTG AGT GCG GTG GAG CGG GCC         100
Leu Thr Pro Met Phe Gly Trp Asn Asn Leu Ser Ala Val Glu Arg Ala
         10                  15                  20

TGG GCA GCC AAC GGC AGC ATG GGG GAG CCC GTG ATC AAG TGC GAG TTC         148
Trp Ala Ala Asn Gly Ser Met Gly Glu Pro Val Ile Lys Cys Glu Phe
     25                  30                  35

GAG AAG GTC ATC AGC ATG GAG TAC ATG GTC TAC TTC AAC TTC TTT GTG         196
Glu Lys Val Ile Ser Met Glu Tyr Met Val Tyr Phe Asn Phe Phe Val
 40                  45                  50                  55

TGG GTG CTG CCC CCG CTT CTC CTC ATG GTC CTC ATC TAC CTG GAG GTC         244
Trp Val Leu Pro Pro Leu Leu Leu Met Val Leu Ile Tyr Leu Glu Val
             60                  65                  70

TTC TAC CTA ATC CGC AAG CAG CTC AAC AAG AAG GTG TCG GCC TCC TCC         292
Phe Tyr Leu Ile Arg Lys Gln Leu Asn Lys Lys Val Ser Ala Ser Ser
         75                  80                  85

GGC GAC CCG CAG AAG TAC TAT GGG AAG GAG CTG AAG ATC GCC AAG TCG         340
Gly Asp Pro Gln Lys Tyr Tyr Gly Lys Glu Leu Lys Ile Ala Lys Ser
     90                  95                 100

CTG GCC CTC ATC CTC TTC CTC TTT GCC CTC AGC TGG CTG CCT TTG CAC         388
Leu Ala Leu Ile Leu Phe Leu Phe Ala Leu Ser Trp Leu Pro Leu His
105                 110                 115

ATC CTC AAC TGC ATC ACC CTC TTC TGC CCG TCC TGC CAC AAG CCC AGC         436
Ile Leu Asn Cys Ile Thr Leu Phe Cys Pro Ser Cys His Lys Pro Ser
120                 125                 130                 135

ATC CTT ACC TAC ATT GCC ATC TTC CTC ACG CAC GGC AAC TCG GCC ATG         484
Ile Leu Thr Tyr Ile Ala Ile Phe Leu Thr His Gly Asn Ser Ala Met
                140                 145                 150

AAC CCC ATT GTC TAT GCC TTC CGC ATC CAG AAG TTC CGC GTC ACC TTC         532
Asn Pro Ile Val Tyr Ala Phe Arg Ile Gln Lys Phe Arg Val Thr Phe
                    155                 160                 165

CTT AAG ATT TGG AAT GAC CAT TTC CGC TGC CAG CCT GCA CCT CCC ATT         580
Leu Lys Ile Trp Asn Asp His Phe Arg Cys Gln Pro Ala Pro Pro Ile
                170                 175                 180

GAC GAG GAT CTC CCA GAA GAG AGG CCT GAT GAC TAGACCCCGC CTTCCGCTCC       633
Asp Glu Asp Leu Pro Glu Glu Arg Pro Asp Asp
185                 190                 195

CACCAGCCCA CATCCAGTGG GGTCTCAGTC CAGTCCTCAC ATGCCGCTG TCCCAGGGGT        693
```

| | | | | | | |
|---|---|---|---|---|---|---|
| CTCCCTGAGC | CTGCCCCAGC | TGGGCTGTTG | GCTGGGGGCA | TGGGGGAGGC | TCTGAAGAGA | 753 |
| TACCCACAGA | GTGTGGTCCC | TCCACTAGGA | GTTAACTACC | CTACACCTCT | GGGCCCTGCA | 813 |
| GGAGGCCTGG | GAGGGCAAGG | GTCCTACGGA | GGGACCAGGT | GTCTAGAGGC | AACAGTGTTC | 873 |
| TGAGCCCCCA | CCTGCCTGAC | CATCCCATGA | GCAGTCCAGC | GCTTCAGGGC | TGGGCAGGTC | 933 |
| CTGGGGAGGC | TGAGACTGCA | GAGGAGCCAC | CTGGGCTGGG | AGAAGGTGCT | TGGGCTTCTG | 993 |
| CGGTGAGGCA | GGGGAGTCTG | CTTGTCTTAG | ATGTTGGTGG | TGCAGCCCCA | GGACCAAGCT | 1053 |
| TAAGGAGAGG | AGAGCATCTG | CTCTGAGACG | GATGGAAGGA | GAGAGGTTGA | GGATGCACTG | 1113 |
| GCCTGTTCTG | TAGGAGAGAC | TGGCCAGAGG | CAGCTAAGGG | GCAGGAATCA | AGGAGCCTCC | 1173 |
| GTTCCCACCT | CTGAGGACTC | TGGACCCCAG | GCCATACCAG | GTGCTAGGGT | GCCTGCTCTC | 1233 |
| CTTGCCCTGG | GCCAGCCCAG | GATTGTACGT | GGGAGAGGCA | GAAAGGGTAG | GTTCAGTAAT | 1293 |
| CATTTCTGAT | GATTTGCTGG | AGTGCTGGCT | CCACGCCCTG | GGGAGTGAGC | TTGGTGCGGT | 1353 |
| AGGTGCTGGC | CTCAAACAGC | CACGAGGTGG | TAGCTCTGAG | CCCTCCTTCT | TGCCCTGAGC | 1413 |
| TTTCGGGGA | GGAGCCTGGA | GTGTAATTAC | CTGTCATCTG | GCCACCAGC | TCCACTGGCC | 1473 |
| CCCGTTGCCG | GGCCTGGACT | GTCCTAGGTG | ACCCCATCTC | TGCTGCTTCT | GGGCCTGATG | 1533 |
| GAGAGGAGAA | CACTAGACAT | GCCAACTCGG | GAGCATTCTG | CCTGCCTGGG | AACGGGGTGG | 1593 |
| ACGAGGGAGT | GTCTGTAAGG | ACTCAGTGTT | GACTGTAGGC | GCCCCTGGGG | TGGGTTTAGC | 1653 |
| AGGCTGCAGC | AGGCAGAGGA | GGAGTACCCC | CCTGAGAGCA | TGTGGGGGAA | GGCCTTGCTG | 1713 |
| TCATGTGAAT | CCCTCAATAC | CCCTAGTATC | TGGCTGGGTT | TTCAGGGGCT | TTGGAAGCTC | 1773 |
| TGTTGCAGGT | GTCCGGGGGT | CTAGGACTTT | AGGGATCTGG | GATCTGGGGA | AGGACCAACC | 1833 |
| CATGCCCTGC | CAAGCCTGGA | GCCCCTGTGT | TGGGGGGCAA | GGTGGGGGAG | CCTGGAGCCC | 1893 |
| CTGTGTGGGA | GGGCGAGGCG | GGGGAGCCTG | GAGCCCCTGT | GTGGGAGGGC | GAGGCGGGGG | 1953 |
| ATCCTGGAGC | CCCTGTGTCG | GGGGGCGAGG | GAGGGGAGGT | GGCCGTCGGT | TGACCTTCTG | 2013 |
| AACATGAGTG | TCAACTCCAG | GACTTGCTTC | CAAGCCCTTC | CCTCTGTTGG | AAATTGGGTG | 2073 |
| TGCCCTGGCT | CCCAAGGGAG | GCCCATGTGA | CTAATAAAAA | ACTGTGAACC | CTGTGGAGAG | 2133 |
| CACATTGCTG | GGCGCCCATC | CCCACCACTG | TTGAGGGCAT | GAAGACA | | 2180 |

( 2 ) INFORMATION FOR SEQ ID NO:4:

( i ) SEQUENCE CHARACTERISTICS:
        ( A ) LENGTH: 194 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ile Leu Ser Phe Val Val Gly Leu Thr Pro Met Phe Gly Trp Asn Asn
 1               5                  10                  15

Leu Ser Ala Val Glu Arg Ala Trp Ala Ala Asn Gly Ser Met Gly Glu
             20                  25                  30

Pro Val Ile Lys Cys Glu Phe Glu Lys Val Ile Ser Met Glu Tyr Met
         35                  40                  45

Val Tyr Phe Asn Phe Phe Val Trp Val Leu Pro Pro Leu Leu Leu Met
     50                  55                  60

Val Leu Ile Tyr Leu Glu Val Phe Tyr Leu Ile Arg Lys Gln Leu Asn
 65                  70                  75                  80

Lys Lys Val Ser Ala Ser Ser Gly Asp Pro Gln Lys Tyr Tyr Gly Lys
             85                  90                  95

Glu Leu Lys Ile Ala Lys Ser Leu Ala Leu Ile Leu Phe Leu Phe Ala
```

|   |   |   |   |   | 100 |   |   |   |   | 105 |   |   |   |   | 110 |   |   |
|---|---|---|---|---|---|---|---|---|---|---|---|---|---|---|---|---|---|
| Leu | Ser | Trp | Leu | Pro | Leu | His | Ile | Leu | Asn | Cys | Ile | Thr | Leu | Phe | Cys |  |  |
|  |  | 115 |  |  |  |  | 120 |  |  |  |  | 125 |  |  |  |  |  |
| Pro | Ser | Cys | His | Lys | Pro | Ser | Ile | Leu | Thr | Tyr | Ile | Ala | Ile | Phe | Leu |  |  |
|  |  | 130 |  |  |  |  | 135 |  |  |  |  | 140 |  |  |  |  |  |
| Thr | His | Gly | Asn | Ser | Ala | Met | Asn | Pro | Ile | Val | Tyr | Ala | Phe | Arg | Ile |  |  |
| 145 |  |  |  |  | 150 |  |  |  |  | 155 |  |  |  |  | 160 |  |  |
| Gln | Lys | Phe | Arg | Val | Thr | Phe | Leu | Lys | Ile | Trp | Asn | Asp | His | Phe | Arg |  |  |
|  |  |  |  | 165 |  |  |  |  | 170 |  |  |  |  | 175 |  |  |  |
| Cys | Gln | Pro | Ala | Pro | Pro | Ile | Asp | Glu | Asp | Leu | Pro | Glu | Glu | Arg | Pro |  |  |
|  |  |  |  | 180 |  |  |  |  | 185 |  |  |  |  | 190 |  |  |  |
| Asp | Asp |  |  |  |  |  |  |  |  |  |  |  |  |  |  |  |  |

( 2 ) INFORMATION FOR SEQ ID NO:5:

( i ) SEQUENCE CHARACTERISTICS:
        ( A ) LENGTH: 2900 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 411..1391

( x i ) SEQUENCE DESCRIPTION: SEQ ID NO:5:

| ATGAGTGTCA | GAAGTGTGAA | GGGTGCCTGT | TCTGAATCCC | AGAGCCTCCT | CTCCCTCTGT | 60 |
|---|---|---|---|---|---|---|
| GAGGCTGGCA | GGTGAGGAAG | GGTTTAACCT | CACTGGAAGG | AATCCCTGGA | GCTAGCGGCT | 120 |
| GCTGAAGGCG | TCGAGGTGTG | GGGGCACTTG | GACAGAACAG | TCAGGCAGCC | GGGAGCTCTG | 180 |
| CCAGCTTTGG | TGACCTTGGG | CCGGGCTGGG | AGCGCTGCGG | CGGGAGCCGG | AGGACTATGA | 240 |
| GCTGCCGCGC | GTTGTCCAGA | GCCCAGCCCA | GCCCTACGCG | CGCGGCCCGG | AGCTCTGTTC | 300 |
| CCTGGAACTT | TGGGCACTGC | CTCTGGGACC | CCTGCCGGCC | AGCAGGCAGG | ATGGTGCTTG | 360 |
| CCTCGTGCCC | CTTGGTGCCC | GTCTGCTGAT | GTGCCCAGCC | TGTGCCCGCC | ATG CCG | 416 |

Met Pro
                                                                                                                                                     1

| CCC | TCC | ATC | TCA | GCT | TTC | CAG | GCC | GCC | TAC | ATC | GGC | ATC | GAG | GTG | CTC | 464 |
|---|---|---|---|---|---|---|---|---|---|---|---|---|---|---|---|---|
| Pro | Ser | Ile | Ser | Ala | Phe | Gln | Ala | Ala | Tyr | Ile | Gly | Ile | Glu | Val | Leu |  |
|  |  | 5 |  |  |  |  | 10 |  |  |  |  | 15 |  |  |  |  |
| ATC | GCC | CTG | GTC | TCT | GTG | CCC | GGG | AAC | GTG | CTG | GTG | ATC | TGG | GCG | GTG | 512 |
| Ile | Ala | Leu | Val | Ser | Val | Pro | Gly | Asn | Val | Leu | Val | Ile | Trp | Ala | Val |  |
|  |  | 20 |  |  |  |  | 25 |  |  |  |  | 30 |  |  |  |  |
| AAG | GTG | AAC | CAG | GCG | CTG | CGG | GAT | GCC | ACC | TTC | TGC | TTC | ATC | GTG | TCG | 560 |
| Lys | Val | Asn | Gln | Ala | Leu | Arg | Asp | Ala | Thr | Phe | Cys | Phe | Ile | Val | Ser |  |
| 35 |  |  |  |  | 40 |  |  |  |  | 45 |  |  |  |  | 50 |  |
| CTG | GCG | GTG | GCT | GAT | GTG | GCC | GTG | GGT | GCC | CTG | GTC | ATC | CCC | CTC | GCC | 608 |
| Leu | Ala | Val | Ala | Asp | Val | Ala | Val | Gly | Ala | Leu | Val | Ile | Pro | Leu | Ala |  |
|  |  |  |  | 55 |  |  |  |  | 60 |  |  |  |  | 65 |  |  |
| ATC | CTC | ATC | AAC | ATT | GGG | CCA | CAG | ACC | TAC | TTC | CAC | ACC | TGC | CTC | ATG | 656 |
| Ile | Leu | Ile | Asn | Ile | Gly | Pro | Gln | Thr | Tyr | Phe | His | Thr | Cys | Leu | Met |  |
|  |  |  | 70 |  |  |  |  | 75 |  |  |  |  | 80 |  |  |  |
| GTT | GCC | TGT | CCG | GTC | CTC | ATC | CTC | ACC | CAG | AGC | TCC | ATC | CTG | GCC | CTG | 704 |
| Val | Ala | Cys | Pro | Val | Leu | Ile | Leu | Thr | Gln | Ser | Ser | Ile | Leu | Ala | Leu |  |
|  |  | 85 |  |  |  |  | 90 |  |  |  |  | 95 |  |  |  |  |
| CTG | GCA | ATT | GCT | GTG | GAC | CGC | TAC | CTC | CGG | GTC | AAG | ATC | CCT | CTC | CGG | 752 |
| Leu | Ala | Ile | Ala | Val | Asp | Arg | Tyr | Leu | Arg | Val | Lys | Ile | Pro | Leu | Arg |  |
|  |  | 100 |  |  |  |  | 105 |  |  |  |  | 110 |  |  |  |  |
| TAC | AAG | ATG | GTG | GTG | ACC | CCC | CGG | AGG | GCG | GCG | GTG | GCC | ATA | GCC | GGC | 800 |

|  |  |  |  |  |  |  |  |  |  |  |  |  |  |  |  |
|---|---|---|---|---|---|---|---|---|---|---|---|---|---|---|---|
| Tyr<br>115 | Lys | Met | Val | Val<br>120 | Thr | Pro | Arg | Arg | Ala<br>125 | Ala | Val | Ala | Ile | Ala | Gly<br>130 |

| TGC | TGG | ATC | CTC | TCC | TTC | GTG | GTG | GGA | CTG | ACC | CCT | ATG | TTT | GGC | TGG | 848 |
|---|---|---|---|---|---|---|---|---|---|---|---|---|---|---|---|---|
| Cys | Trp | Ile | Leu | Ser<br>135 | Phe | Val | Val | Gly | Leu<br>140 | Thr | Pro | Met | Phe | Gly<br>145 | Trp |  |

| AAC | AAT | CTG | AGT | GCG | GTG | GAG | CGG | GCC | TGG | GCA | GCC | AAC | GGC | AGC | ATG | 896 |
|---|---|---|---|---|---|---|---|---|---|---|---|---|---|---|---|---|
| Asn | Asn | Leu | Ser<br>150 | Ala | Val | Glu | Arg | Ala<br>155 | Trp | Ala | Ala | Asn | Gly<br>160 | Ser | Met |  |

| GGG | GAG | CCC | GTG | ATC | AAG | TGC | GAG | TTC | GAG | AAG | GTC | ATC | AGC | ATG | GAG | 944 |
|---|---|---|---|---|---|---|---|---|---|---|---|---|---|---|---|---|
| Gly | Glu | Pro<br>165 | Val | Ile | Lys | Cys | Glu<br>170 | Phe | Glu | Lys | Val | Ile<br>175 | Ser | Met | Glu |  |

| TAC | ATG | GTC | TAC | TTC | AAC | TTC | TTT | GTG | TGG | GTG | CTG | CCC | CCG | CTT | CTC | 992 |
|---|---|---|---|---|---|---|---|---|---|---|---|---|---|---|---|---|
| Tyr | Met<br>180 | Val | Tyr | Phe | Asn | Phe<br>185 | Phe | Val | Trp | Val | Leu<br>190 | Pro | Pro | Leu | Leu |  |

| CTC | ATG | GTC | CTC | ATC | TAC | CTG | GAG | GTC | TTC | TAC | CTA | ATC | CGC | AAG | CAG | 1040 |
|---|---|---|---|---|---|---|---|---|---|---|---|---|---|---|---|---|
| Leu<br>195 | Met | Val | Leu | Ile | Tyr<br>200 | Leu | Glu | Val | Phe | Tyr<br>205 | Leu | Ile | Arg | Lys | Gln<br>210 |  |

| CTC | AAC | AAG | AAG | GTG | TCG | GCC | TCC | TCC | GGC | GAC | CCG | CAG | AAG | TAC | TAT | 1088 |
|---|---|---|---|---|---|---|---|---|---|---|---|---|---|---|---|---|
| Leu | Asn | Lys | Lys | Val<br>215 | Ser | Ala | Ser | Ser | Gly<br>220 | Asp | Pro | Gln | Lys | Tyr<br>225 | Tyr |  |

| GGG | AAG | GAG | CTG | AAG | ATC | GCC | AAG | TCG | CTG | GCC | CTC | ATC | CTC | TTC | CTC | 1136 |
|---|---|---|---|---|---|---|---|---|---|---|---|---|---|---|---|---|
| Gly | Lys | Glu | Leu<br>230 | Lys | Ile | Ala | Lys | Ser<br>235 | Leu | Ala | Leu | Ile | Leu<br>240 | Phe | Leu |  |

| TTT | GCC | CTC | AGC | TGG | CTG | CCT | TTG | CAC | ATC | CTC | AAC | TGC | ATC | ACC | CTC | 1184 |
|---|---|---|---|---|---|---|---|---|---|---|---|---|---|---|---|---|
| Phe | Ala | Leu | Ser<br>245 | Trp | Leu | Pro | Leu | His<br>250 | Ile | Leu | Asn | Cys<br>255 | Ile | Thr | Leu |  |

| TTC | TGC | CCG | TCC | TGC | CAC | AAG | CCC | AGC | ATC | CTT | ACC | TAC | ATT | GCC | ATC | 1232 |
|---|---|---|---|---|---|---|---|---|---|---|---|---|---|---|---|---|
| Phe | Cys | Pro<br>260 | Ser | Cys | His | Lys | Pro<br>265 | Ser | Ile | Leu | Thr | Tyr<br>270 | Ile | Ala | Ile |  |

| TTC | CTC | ACG | CAC | GGC | AAC | TCG | GCC | ATG | AAC | CCC | ATT | GTC | TAT | GCC | TTC | 1280 |
|---|---|---|---|---|---|---|---|---|---|---|---|---|---|---|---|---|
| Phe<br>275 | Leu | Thr | His | Gly | Asn<br>280 | Ser | Ala | Met | Asn | Pro<br>285 | Ile | Val | Tyr | Ala | Phe<br>290 |  |

| CGC | ATC | CAG | AAG | TTC | CGC | GTC | ACC | TTC | CTT | AAG | ATT | TGG | AAT | GAC | CAT | 1328 |
|---|---|---|---|---|---|---|---|---|---|---|---|---|---|---|---|---|
| Arg | Ile | Gln | Lys | Phe<br>295 | Arg | Val | Thr | Phe | Leu<br>300 | Lys | Ile | Trp | Asn | Asp<br>305 | His |  |

| TTC | CGC | TGC | CAG | CCT | GCA | CCT | CCC | ATT | GAC | GAG | GAT | CTC | CCA | GAA | GAG | 1376 |
|---|---|---|---|---|---|---|---|---|---|---|---|---|---|---|---|---|
| Phe | Arg | Cys | Gln | Pro<br>310 | Ala | Pro | Pro | Ile | Asp<br>315 | Glu | Asp | Leu | Pro | Glu<br>320 | Glu |  |

| AGG | CCT | GAT | GAC | TAGACCCCGC | CTTCCGCTCC | CACCAGCCCA | CATCCAGTGG | 1428 |
|---|---|---|---|---|---|---|---|---|
| Arg | Pro | Asp | Asp |  |  |  |  |  |
|  |  | 325 |  |  |  |  |  |  |

| GGTCTCAGTC | CAGTCCTCAC | ATGCCCGCTG | TCCCAGGGGT | CTCCCTGAGC | CTGCCCCAGC | 1488 |
|---|---|---|---|---|---|---|
| TGGGCTGTTG | GCTGGGGGCA | TGGGGGAGGC | TCTGAAGAGA | TACCCACAGA | GTGTGGTCCC | 1548 |
| TCCACTAGGA | GTTAACTACC | CTACACCTCT | GGGCCCTGCA | GGAGGCCTGG | GAGGGCAAGG | 1608 |
| GTCCTACGGA | GGGACCAGGT | GTCTAGAGGC | AACAGTGTTC | TGAGCCCCCA | CCTGCCTGAC | 1668 |
| CATCCCATGA | GCAGTCCAGC | GCTTCAGGGC | TGGGCAGGTC | CTGGGGAGGC | TGAGACTGCA | 1728 |
| GAGGAGCCAC | CTGGGCTGGG | AGAAGGTGCT | TGGGCTTCTG | CGGTGAGGCA | GGGGAGTCTG | 1788 |
| CTTGTCTTAG | ATGTTGGTGG | TGCAGCCCCA | GGACCAAGCT | TAAGGAGAGG | AGAGCATCTG | 1848 |
| CTCTGAGACG | GATGGAAGGA | GAGAGGTTGA | GGATGCACTG | GCCTGTTCTG | TAGGAGAGAC | 1908 |
| TGGCCAGAGG | CAGCTAAGGG | GCAGGAATCA | AGGAGCCTCC | GTTCCCACCT | CTGAGGACTC | 1968 |
| TGGACCCCAG | GCCATACCAG | GTGCTAGGGT | GCCTGCTCTC | CTTGCCCTGG | GCCAGCCCAG | 2028 |
| GATTGTACGT | GGGAGAGGCA | GAAAGGGTAG | GTTCAGTAAT | CATTTCTGAT | GATTTGCTGG | 2088 |
| AGTGCTGGCT | CCACGCCCTG | GGGAGTGAGC | TTGGTGCGGT | AGGTGCTGGC | CTCAAACAGC | 2148 |
| CACGAGGTGG | TAGCTCTGAG | CCCTCCTTCT | TGCCCTGAGC | TTTCCGGGGA | GGAGCCTGGA | 2208 |
| GTGTAATTAC | CTGTCATCTG | GGCCACCAGC | TCCACTGGCC | CCCGTTGCCG | GGCCTGGACT | 2268 |

```
GTCCTAGGTG ACCCCATCTC TGCTGCTTCT GGGCCTGATG GAGAGGAGAA CACTAGACAT      2328

GCCAACTCGG GAGCATTCTG CCTGCCTGGG AACGGGGTGG ACGAGGGAGT GTCTGTAAGG      2388

ACTCAGTGTT GACTGTAGGC GCCCCTGGGG TGGGTTTAGC AGGCTGCAGC AGGCAGAGGA      2448

GGAGTACCCC CCTGAGAGCA TGTGGGGGAA GGCCTTGCTG TCATGTGAAT CCCTCAATAC      2508

CCCTAGTATC TGGCTGGGTT TTCAGGGGCT TTGGAAGCTC TGTTGCAGGT GTCCGGGGGT      2568

CTAGGACTTT AGGGATCTGG GATCTGGGGA AGGACCAACC CATGCCCTGC CAAGCCTGGA      2628

GCCCCTGTGT TGGGGGGCAA GGTGGGGGAG CCTGGAGCCC CTGTGTGGGA GGGCGAGGCG      2688

GGGGAGCCTG GAGCCCCTGT GTGGGAGGGC GAGGCGGGGG ATCCTGGAGC CCCTGTGTCG      2748

GGGGGCGAGG GAGGGGAGGT GGCCGTCGGT TGACCTTCTG AACATGAGTG TCAACTCCAG      2808

GACTTGCTTC CAAGCCCTTC CCTCTGTTGG AAATTGGGTG TGCCCTGGCT CCCAAGGGAG      2868

GCCCATGTGA CTAATAAAAA ACTGTGAACC CT                                    2900
```

( 2 ) INFORMATION FOR SEQ ID NO:6:

( i ) SEQUENCE CHARACTERISTICS:
        ( A ) LENGTH: 326 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Pro Pro Ser Ile Ser Ala Phe Gln Ala Ala Tyr Ile Gly Ile Glu
 1               5                  10                  15

Val Leu Ile Ala Leu Val Ser Val Pro Gly Asn Val Leu Val Ile Trp
            20                  25                  30

Ala Val Lys Val Asn Gln Ala Leu Arg Asp Ala Thr Phe Cys Phe Ile
        35                  40                  45

Val Ser Leu Ala Val Ala Asp Val Ala Val Gly Ala Leu Val Ile Pro
    50                  55                  60

Leu Ala Ile Leu Ile Asn Ile Gly Pro Gln Thr Tyr Phe His Thr Cys
65                  70                  75                  80

Leu Met Val Ala Cys Pro Val Leu Ile Leu Thr Gln Ser Ser Ile Leu
                85                  90                  95

Ala Leu Leu Ala Ile Ala Val Asp Arg Tyr Leu Arg Val Lys Ile Pro
            100                 105                 110

Leu Arg Tyr Lys Met Val Val Thr Pro Arg Arg Ala Ala Val Ala Ile
        115                 120                 125

Ala Gly Cys Trp Ile Leu Ser Phe Val Val Gly Leu Thr Pro Met Phe
    130                 135                 140

Gly Trp Asn Asn Leu Ser Ala Val Glu Arg Ala Trp Ala Ala Asn Gly
145                 150                 155                 160

Ser Met Gly Glu Pro Val Ile Lys Cys Glu Phe Glu Lys Val Ile Ser
                165                 170                 175

Met Glu Tyr Met Val Tyr Phe Asn Phe Phe Val Trp Val Leu Pro Pro
            180                 185                 190

Leu Leu Leu Met Val Leu Ile Tyr Leu Glu Val Phe Tyr Leu Ile Arg
        195                 200                 205

Lys Gln Leu Asn Lys Lys Val Ser Ala Ser Ser Gly Asp Pro Gln Lys
    210                 215                 220

Tyr Tyr Gly Lys Glu Leu Lys Ile Ala Lys Ser Leu Ala Leu Ile Leu
225                 230                 235                 240

Phe Leu Phe Ala Leu Ser Trp Leu Pro Leu His Ile Leu Asn Cys Ile
                245                 250                 255
```

| Thr | Leu | Phe | Cys | Pro | Ser | Cys | His | Lys | Pro | Ser | Ile | Leu | Thr | Tyr | Ile |
|---|---|---|---|---|---|---|---|---|---|---|---|---|---|---|---|
| | | | 260 | | | | | 265 | | | | | 270 | | |

| Ala | Ile | Phe | Leu | Thr | His | Gly | Asn | Ser | Ala | Met | Asn | Pro | Ile | Val | Tyr |
|---|---|---|---|---|---|---|---|---|---|---|---|---|---|---|---|
| | | 275 | | | | | 280 | | | | | 285 | | | |

| Ala | Phe | Arg | Ile | Gln | Lys | Phe | Arg | Val | Thr | Phe | Leu | Lys | Ile | Trp | Asn |
|---|---|---|---|---|---|---|---|---|---|---|---|---|---|---|---|
| | 290 | | | | | | 295 | | | | 300 | | | | |

| Asp | His | Phe | Arg | Cys | Gln | Pro | Ala | Pro | Pro | Ile | Asp | Glu | Asp | Leu | Pro |
|---|---|---|---|---|---|---|---|---|---|---|---|---|---|---|---|
| 305 | | | | | 310 | | | | | 315 | | | | | 320 |

| Glu | Glu | Arg | Pro | Asp | Asp |
|---|---|---|---|---|---|
| | | | | 325 | |